(12) United States Patent
Teague et al.

(10) Patent No.: US 11,554,083 B2
(45) Date of Patent: Jan. 17, 2023

(54) DHA AS A HAIR COLOURANT

(71) Applicant: Vivimed Specialty Chemicals UK Limited, Huddersfield (GB)

(72) Inventors: Jennie Teague, Huddersfield (GB); Katie Hardie, Huddersfield (GB)

(73) Assignee: JAMES ROBINSON GROUP LTD

( * ) Notice: Subject to any disclaimer, the term of this patent is extended or adjusted under 35 U.S.C. 154(b) by 264 days.

(21) Appl. No.: 16/923,721

(22) Filed: Jul. 8, 2020

(65) Prior Publication Data
US 2021/0346258 A1 Nov. 11, 2021

(51) Int. Cl.
| | |
|---|---|
| *A61Q 5/10* | (2006.01) |
| *A61K 8/35* | (2006.01) |
| *A45D 7/02* | (2006.01) |
| *A61Q 5/06* | (2006.01) |
| *A45D 2/00* | (2006.01) |
| *A45D 2/36* | (2006.01) |
| *A45D 19/00* | (2006.01) |

(52) U.S. Cl.
CPC .................. *A61K 8/35* (2013.01); *A45D 7/02* (2013.01); *A61Q 5/065* (2013.01); *A61Q 5/10* (2013.01); *A45D 2/001* (2013.01); *A45D 2/002* (2013.01); *A45D 2/367* (2013.01); *A45D 19/0066* (2021.01); *A45D 2200/25* (2013.01)

(58) Field of Classification Search
CPC . A61Q 5/10; A61Q 5/065; A61K 8/35; A45D 19/0066; A45D 2/002; A45D 2200/25
USPC ............................................................ 8/405
See application file for complete search history.

(56) References Cited

U.S. PATENT DOCUMENTS

| | | | |
|---|---|---|---|
| 2005/0210606 A1* | 9/2005 | Wilz ........................ | A61K 8/35 8/405 |
| 2019/0240133 A1* | 8/2019 | Schrott .................. | A61K 8/604 |
| 2020/0038303 A1 | 2/2020 | Degeorge et al. | |

FOREIGN PATENT DOCUMENTS

| | | |
|---|---|---|
| DE | 10118894 | 10/2002 |
| TW | 201125591 | 8/2011 |
| WO | 2012084533 | 6/2012 |
| WO | 2019042795 | 3/2019 |

* cited by examiner

*Primary Examiner* — Eisa B Elhilo
(74) *Attorney, Agent, or Firm* — K&L Gates LLP

(57) ABSTRACT

There is described a method for colouring hair, said method comprising treating hair with a composition comprising dihydroxyacetone (DHA), in free form or in salt form; optionally drying the hair; and heating the treated hair, including the applied DHA composition, to a temperature of from about 100° C. to about 250° C.

17 Claims, No Drawings

DHA AS A HAIR COLOURANT

CROSS REFERENCE TO RELATED APPLICATIONS

This application claims priority from Great Britain Patent Application GB 2006790.6, filed on May 7, 2020, the entire disclosure of which is incorporated by reference herein.

FIELD OF THE INVENTION

The present invention relates to a method for colouring hair comprising the use of dihydroxyacetone (DHA) as a hair colourant; and compositions and uses related thereto.

More particularly, this invention relates to the use of dihydroxyacetone (DHA), with heat, as a hair colourant and methods and compositions related thereto.

BACKGROUND OF THE INVENTION

Dihydroxyacetone (DHA) has been known to be used as a skin colouring agent in sunless tanning skincare preparations since the 1950s. However, DHA is not a dye, stain or paint, but is known to cause a chemical reaction with the amino acids in the protein keratin, the major component of the skin surface. One of the pathways of this chemical reaction is a conventional or free radical-mediated Maillard reaction. The conventional Maillard reaction is a process well known to food chemists that causes the browning that occurs during food manufacturing and storage. It does not involve the underlying skin pigmentation. Furthermore, the colour effect is temporary and fades gradually over 3 to 10 days.

DHA is used in a number of hair care products, usually as a colour intensifier, e.g. in oxidative hair coloration or as a stiffener in hair shaping products.

For example, European Patent Application No. EP 1250908 describes a composition for dyeing human hair comprising an oxidation dyestuff precursor, such as, 1,4-diaminobenzene, and 0.01% to 10% w/w of dihydroxyacetone as an oxidising agent.

US Patent application No. 2005/0210606 describes a pre-treatment composition for oxidative colouring of human hair comprising dihydroxyacetone at a concentration of 0.1 to 20% by weight. It describes the use of DHA added as a colour intensifier in oxidative hair colouration wherein a composition comprising DHA is applied onto hair before bringing compositions comprising mixture of oxidation dyestuffs precursors and/or couplers and an oxidizing agent onto the hair.

Taiwanese Patent application No. TW 2011/25591 describes a natural hair dye which comprises a dye and from 0.001 to 50 wt % DHA.

The disclosure of TW 201125591 provides instructions for application of the natural hair dye, which comprises spreading the natural hair dye evenly on the hair; then using hot air from a hair dryer (above 50° C.) to blow the hair coated with natural hair dye to complete the colour enhancement and colour supplement effect. Conventionally, a hair dryer, can generally reach about 60° C. when set on the highest setting.

US Patent application No. 2020/0038303 describes a method for colouring hair, including applying an aqueous colouring composition and heat to the hair wherein the colouring composition includes water and one or more colourants for colouring the hair. After application of the aqueous colouring composition to the hair, the hair having the colouring composition applied thereon is heated to a temperature of about 100° C. to 200° C. The aqueous colouring composition comprising one or more direct dyes selected from nitro-phenylenediamines, nitro-aminophenols, azo dyes, anthraquinones, triarylmethane dyes and indophenols. The disclosure of US '303 makes no mention of DHA.

We have now found a new and improved method of colouring hair.

SUMMARY OF THE INVENTION

The method of the present invention reduce the processing time for hair colouring and also removes or minimises the need for expensive conventional hair dyes.

Thus, according a first aspect of the invention there is provided a method for colouring hair, said method comprising treating hair with a composition comprising dihydroxyacetone (DHA), in free form or in salt form; optionally drying the hair; and heating the treated hair, including the applied DHA composition, to a temperature of from about 100° C. to about 250° C.

The DHA composition can be applied to all of the hair of the head or may be applied to select portions of the hair. The DHA composition can be applied to dry hair, wet hair or damp hair. For example, the hair may be shampooed or rinsed prior to the application of the DHA composition.

After applying a sufficient amount of the DHA composition to the hair to be coloured, the treated hair (and the applied DHA composition) is heated. The heat may be applied quickly after application of the DHA composition to the hair so that the entire colouring process is as fast as possible. However, preferably the treated hair is dried by any conventional means prior to applying the heat. Alternatively the hair may be allowed to dry naturally prior to the application of heat. The hair may also be heat treated sometime after drying with a hair dryer, prior to the first wash. Typically the heat applied to the DHA treated hair within about 5 minutes after application of the DHA composition to the hair. Similarly, the heat may be applied to the treated hair within 4 minutes, within 3 minutes, within 2 minutes, or within 1 minute after application of the DHA composition.

The treated hair may be heated to a temperature of from about 100° C. to about 250° C. The extent of the colour may vary depending upon the temperature. The first colour change occurs at about 100-120° C., darkening occurs with increased temperature. Thus, the treated hair may be heated to a temperature of from about 120° C. to about 240° C.; or from about 150° C. to about 240° C.; or from about 200° C. to about 240° C.; or from about 210° C. to about 240° C.; or from about 220° C. to about 240° C.; or from about 230° C. to about 240° C.; or a temperature of about 240° C.

The treatment time, i.e. the time that DHA is in contact with the hair, may vary. Generally, a longer treatment time is required when heating hair to a lower temperature. Thus, the method according to the invention may comprise a treatment time (DHA treatment time) of from about 1 second to 60 minutes, preferably 1 second to 5 minutes, preferably 3 seconds to 3 minutes.

Furthermore, the method according to the invention may comprise a heating time (heating the DHA treated hair) of from about 1 second to about 30 minutes, preferably, from about 1 second to about 5 minutes, preferably from about 3 seconds to about 1 minute.

The heating of the treated hair may be carried out using any conventionally known means that will achieve the desired temperature of from about 100° C. to about 250° C. For example, a conventional hair dryer could be expected to achieve a temperature of about 50° C. to 60° C. Such temperatures are unsuitable for the method of the present invention. Thus, for example, a hot iron, such as, a curling iron, a straightening iron, or a hot comb may be used to apply heat to the treated hair. This is a particularly efficient way to rapidly heat the hair for a period of time. It will be understood that other methods of heating the hair may also be considered, for example, other methods include, but shall not be limited to, wrapping the treated hair in a plastic wrap or covered with a plastic cap and applying heat (for example, hot air, a heated pad, etc.), wrapping the treated hair in a heat-conducting foil, for example, an aluminium foil, and applying heat (for example, hot air, a heated pad, a hot iron). In some cases, the DHA composition may be applied to one or more sections of hair and a foil may be used to wrap (e.g., sandwich) the sections of hair.

After the heating is complete, the hair may optionally be rinsed or shampooed as desired. This removes any remnants of the DHA composition that remain on the hair after heating, and leaves behind the freshly coloured hair. The hair may be subsequently dried, and styled as desired.

Dihydroxyacetone (DHA) is a white to off-white, crystalline powder which can exist as a mixture of monomers and dimers. In the solid crystalline state the dimers predominate, but upon heating or melting, the dimers break down to yield the monomers. This conversion of the dimeric form to the monomeric form also occurs in aqueous solution. Dihydroxyacetone is also known to be more stable at acidic pH values. DHA may also exist in salt form and the use of such salt forms of DHA is included within the scope of the present invention. As used herein, the term "salts" refers to salts that retain the effectiveness and properties of the DHA of the invention and, which are not otherwise undesirable. Acceptable salts include, but shall not be limited to, alkali metal salts, such as, sodium or potassium salts. Additional suitable salts can be found, for example, in "Handbook of Pharmaceutical Salts: Properties, Selection, and Use" by Stahl and Wermuth (Wiley-VCH, Weinheim, Germany, 2002).

Hitherto, the use of DHA or a composition comprising DHA, in free form or in salt form, as a hair colourant, with applied heat, has not been known. Therefore, according to a further aspect of the invention there is provided the use of DHA, in free form or in salt form, as a hair colourant.

According to this aspect of the invention, there is especially provided the use of DHA, in free form or in salt form, as a thermally activated hair colourant.

According to a yet further aspect of the invention there is provided the use of a composition comprising DHA, in free form or in salt form, as a hair colourant. In particular, this aspect of the invention provides the use of composition comprising DHA, in free form or in salt form, as a thermally activated hair colourant.

The amount of DHA, in free form or in salt form, present in the composition may vary, depending upon, inter alia, the nature of the hair, the tone of the hair colouring, etc.

Generally the amount of DHA present in the composition will be from about 1 to about 20% w/w, preferably from about 2 to about 15% w/w, preferably from about 2 to about 10% w/w, preferably from about 4 to about 10 w/w, preferably from about 4 to about 8% w/w, preferably from about 4 to about 6% w/w.

The DHA composition will generally be an aqueous solution. Alternatively, the DHA composition may be used in an oil based product.

The DHA composition will comprise a composition for topical application to the hair. Such a composition may generally be classified as leave-on or rinse off composition. The DHA composition may be in the form of a spray, a gel, a lotion, a cream, a paste or a foam. A spray can be useful because the DHA composition can be applied directly to the hair without requiring any utensils such as a brush, although it may be desirable to comb or brush the aqueous hair colouring composition throughout the hair prior to heating to ensure that the DHA composition penetrates and coats the hair. A DHA composition in the form of a gel, lotion, cream, paste or foam can be useful in preventing unwanted running or dripping of the colouring composition from the hair. Examples of such compositions include, but shall not be limited to leave-on hair lotions, creams, and wash-off shampoos, conditioners, and the like.

The DHA composition is preferably in the form of a spray.

The composition of the invention and the use of the composition as herein described is advantageous in that, inter alia, when used to treat hair and accompanied with heat, it provides a rapid hair colourant; and may be used without the need for additional colourants, e.g. synthetic dyes used in conventional hair colouring formulae.

However, it is within the scope of the present invention for the DHA composition to include one or more additional hair colourants. The use of an additional hair colourant may be desirable, inter alia, to provide a specific colour, tone, etc.

According to this aspect of the invention DHA composition may include one or more colourants. Examples of such colourants include oxidative dyes, direct dyes, direct action dyes, natural dyes, metallic dyes, reactive dyes and mixtures thereof.

The term "natural dye" means any dye or dye precursor that is naturally occurring and that is produced either by extraction (and possible purification) from a plant matrix optionally in the presence of natural compounds such as ash or ammonia, or via chemical synthesis.

Natural dyes that may be mentioned include, but shall not be limited to, one or more of alizarin, apigenidin, betanin, bixin, carminic acid, catechin, chlorophyllin, chromene dyes and chroman dyes, curcumin, epicatechin, henna, indigo, isatin, juglone, kermesic acid, laccaic acid, lawsone, orceins, polyphenols or ortho-diphenols (ODPs), purpurin, purpurogallin, quercetin, sorghum, spinulosin and Tyrian purple.

Examples oxidative dyes include, but shall not be limited to, para-phenylenediamines, bis(phenyl)alkylenediamines, para-aminophenols, ortho-aminophenols and heterocyclic bases, and the addition salts thereof. In general, the addition salts of the oxidative dyes may be selected from the addition salts with an acid such as the hydrochlorides, hydrobromides, sulfates, citrates, succinates, tartrates, lactates, tosylates, benzenesulfonates, phosphates and acetates.

The para-phenylenediamines that may be mentioned include, but shall not be limited to, para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(.beta.-hydroxyethyl)-para-phenylenediamine, 4-N,N-bis(.beta.-hydroxyethyl)amino-2-methylaniline, 4-N,N-bis(.beta.-hydroxyethyl)amino-2-chloroaniline, 2-.beta.-hydroxyethyl-para-phenylenediamine, 2-methoxymethyl-para-phenylenediamine, 2-fluoro-para-phenylenediamine, 2-isopropyl-para-phenylenediamine, N-(.beta-hydroxypropyl)-para-phenylenediamine, 2-hydroxymethyl-para-phenylenediamine, N,N-dimethyl-3-methyl-para-phenylenediamine, N-ethyl-N-(.beta.-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(3-hydroxyethyloxy-para-phenylenediamine, 2-β-acetylaminoethyloxy-para-phenylenediamine, N-(D-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

The bis(phenyl)alkylenediamines that may be mentioned, include, but shall not be limited to, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

The para-aminophenols that may be mentioned include, but shall not be limited to, para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

The ortho-aminophenols that may be mentioned include, but shall not be limited to, 2-aminophenol, 2-amino-5-methylphenol, 2-amino-6-methylphenol and 5-acetamido-2-aminophenol, and the addition salts thereof.

The heterocyclic bases that may be mentioned include, but shall not be limited to, pyridine derivatives, pyrimidine derivatives and pyrazole derivatives.

The pyridine derivatives that may be mentioned include, but shall not be limited to, the compounds such as 2,5-diaminopyridine, 2-(4-methoxyphenyl)amino-3-aminopyridine and 3,4-diaminopyridine, and the addition salts thereof. Other pyridine oxidative dyes that are useful in the present disclosure are the 3-aminopyrazolo[1,5-a]pyridine oxidative dyes or the addition salts thereof. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-.quadrature.-hydroxyethoxy-3-amino-pyrazolo[1,5-a]pyridine; 2-(4-dimethylpyperazinium-1-yl)-3-amino-pyrazolo[1,5-a]pyridine; and the addition salts thereof.

The pyrimidine derivatives that may be mentioned include, but shall not be limited to, compounds such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

The pyrazole derivatives that may be mentioned include, but shall not be limited to, compounds such as 4,5-diamino-1-methyl-pyrazole, 4,5-diamino-1-(β-hydroxyethyl)pyrazole, 3,4-diamino-pyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(3-hydroxyethyl)-3-methylpyrazole, 4,5-diamino-1-ethyl-3-methyl-pyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. 4,5-Diamino-1-(p-methoxyethyl)pyrazole may also be used.

Pyrazole derivatives that may also be mentioned include, but shall not be limited to, diamino-N,N-dihydropyrazolopyrazolones such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one. 2,3-Diamino-6,7-dihydro-1H,5H-pyrazolo[1,2-a]pyrazol-1-one and/or salts thereof.

Examples of direct dyes include, but shall not be limited to, nitro-phenylenediamines, nitro-aminophenols, azo dyes, anthraquinones, triarylmethane dyes, and indophenols. The direct dyes may be cationic dyes, anionic dyes, nitro dyes, or a mixture thereof.

Examples of cationic dyes include, but shall not be limited to, Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green, Basic Orange 31, 1, Basic Red 2, Basic Red 12 Basic Red 22, Basic Red 76 Basic Red 51, Basic Violet 1, Basic Violet 2, Basic Violet 3, Basic Violet 10, Basic Violet 14, Basic Yellow 57 and Basic Yellow 87.

Examples anionic dyes include, but shall not be limited to, Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium and/or potassium.

Examples of nitro dyes include, but shall not be limited to, HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue No. 17, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

In addition the DHA composition may optionally include one or more water-soluble solvents. Examples of such solvents include glycerin, mono-alcohols, polyols (polyhydric alcohols), glycols, and mixtures thereof. In some instances, one or more mono-alcohol may be included, for example, isopropyl alcohol.

The term "water-soluble solvent" should be construed as a compound that has a solubility of at least 50% in water (at 25° C. and at atmospheric pressure (760 mmHg)). In some cases, the water-soluble solvent has a solubility of at least 60%, 70%, 80%, or 90%. Examples of water-soluble solvents include glycerin, alcohols (e.g. C1-8 or C1-4 alcohols), organic solvents, polyols, glycols, and a mixture thereof.

Examples of water-soluble solvents include lower mono-alcohols and monomeric polyols. Examples of lower mono-alcohols are those containing from 1 to 5 carbon atoms, such as ethanol and isopropanol, glycols containing from 2 to 8 carbon atoms, such as ethylene glycol, propylene glycol, 1,3-butylene glycol and dipropylene glycol, C3 and C4 ketones and C2-C4 aldehydes.

Examples of water-soluble organic solvents that may be mentioned include linear or branched C2-C4 alkanols, such as ethanol and isopropanol; polyols and polyol ethers, for instance 2-butoxyethanol, glycerol, propylene glycol, dipropylene glycol, polyethylene glycols, propylene glycol monomethyl ether, diethylene glycol monomethyl ether and monoethyl ether, and also aromatic alcohols, for instance benzyl alcohol or phenoxyethanol, and mixtures thereof.

The water-soluble solvent may include one or more monomeric polyols. Examples of monomeric polyols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, 1,6-hexanediol, 2-methyl-2,4-pentanediol, polyethylene glycol, 1,2,4-butanetriol, and 1,2,6-hexanetriol. Non-limiting examples of monomeric polyols having one or more aliphatic diols include 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and mixtures thereof.

The total amount of the water-soluble solvent in the DHA compositions, if present, can vary but is typically about 0.1 to about 50% w/w, based on the total weight of the aqueous hair colouring composition. The total amount of the water-soluble solvent may be about 0.1 to about 25% w/w, about 0.1 to about 15% w/w, about 0.1 to about 10% w/w, about 1 to about 50% w/w, about 1 to about 25% w/w, about 1 to about 15% w/w, or about 1 to about 10% w/w, based on the total weight of the DHA composition.

The DHA composition may optionally include one or more thickening agents. Thickening agents are useful for adjusting or increasing the viscosity of the DHA compositions. Examples of thickening agents include carboxylic acid polymers, crosslinked polyacrylate polymers, polyacrylamide polymers, polysaccharides, gums, and a mixture thereof. In some cases, polysaccharide thickening agents. Examples include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Tickening agents include xanthan gum, guar gum, biosaccharide gum, cellulose, acacia Seneca gum, sclerotium gum, agarose, pechtin, gellan gum, hyaluronic acid. In some instances, the one or more thickening agents may include polymeric thickening agents, for example, those selected from the group consisting of ammonium polyacryloyldimethyl taurate, ammonium acryloyldimethyltaurate/VP copolymer, sodium polyacrylate, acrylates copolymers, polyacrylamide, carbomer, acrylates/C10-30 alkyl acrylate crosspolymer, and acrylamidelsodium acryloyldimethyltaurate copolymer.

The total amount of thickening agents in the DHA composition, if present, may vary but is typically about 0.1 to about 10% w/w, based on the total weight of the DHA composition. The total amount of thickening agents may be about 0.1 to about 8% w/w, about 0.1 to about 5% w/w, about 0.5 to about 10% w/w, about 0.5 to about 8% w/w, about 0.5 to about 5% w/w about 1 to about 10% w/w, about 1 to about 8% w/w, or about 1 to about 5% w/w, based on the total weight of the DHA composition.

The DHA composition may optionally include one or more non-silicone fatty compounds. Examples of non-silicone fatty compounds include oils, mineral oil, alkanes (paraffins), fatty alcohols, fatty acids, fatty alcohol derivatives, fatty acid derivatives, esters of fatty alcohols, hydroxy-substituted fatty acids, waxes, triglyceride compounds, lanolin, and a mixture thereof.

The total amount of the non-silicone fatty compounds, if present, may vary but is typically about 0.01 to about 45% w/w, based on the total weight of the DHA composition. In some instance, the total amount of the non-silicone fatty compounds is about 0.01 to about 40% w/w, about 0.01 to about 25% w/w, about 0.01 to about 10% w/w, about 0.1 to about 45% w/w, about 0.1 to about 40% w/w, about 0.1 to about 25% w/w, about 0.1 to about 10% w/w, about 1 to about 45% w/w, about 1 to about 40% w/w, about 1 to about 25% w/w, about 1 to about 10% w/w, based on the total weight of the DHA composition.

One or more surfactants may optionally be included in the DHA composition. Surfactants may be cationic, anionic, nonionic, or amphoteric/zwitterionic. In some instances, the DHA composition includes one or more cationic surfactants and/or one or more nonionic surfactants.

Examples of cationic surfactants include behentrimonium chloride, cetrimonium chloride, and guar hydroxypropyltrimonium chloride.

The total amount of the surfactant(s) in the DHA composition, if present, may vary but may be about 0.01 to about 10% w/w, based on the total weight of the DHA composition. In some cases, the total amount of surfactant(s) in the DHA composition, if present, is about 0.01 to about 8% w/w, about 0.01 to about 5% w/w, about 1 to about 10% w/w, about 1 to about 8% w/w, about 1 to about 6% w/w, or about 1 to about 5% w/w, based on the total weight of the DHA composition.

One or more silicones may optionally be included in the DHA composition. Examples of silicones include polyorganosiloxanes, polyalkylsiloxanes, polyarylsiloxanes, polyalkarylsiloxanes, polyestersiloxanes, and a mixture thereof. Suitable examples of silicones include dimethicone, cyclomethicone, amodimethicone, trimethyl silyl amodimethicone, phenyl trimethicone, trimethyl siloxy silicate, and mixtures thereof.

The total amount of the one or more silicones may vary but is typically about 0.01 to about 20% w/w, based on the total weight of the DHA composition. In some cases, the total amount of the one or more silicones is about 0.01 to about 15% w/w, 0.01 to about 10% w/w, about 0.01 to about 8% w/w, about 0.01 to about 5% w/w, about 0.1 to about 20% w/w, about 0.1 to about 15% w/w, about 0.1 to about 10% w/w, or about 0.1 to about 5% w/w, based on the total weight of the DHA composition.

The pH of the DHA compositions can vary greatly, for example, from about 2 to about 12, about 3 to about 11, or about 4 to about 10. In some instances, it may be preferable to have an acidic DHA composition having pH, for example, of about 2 to below 7, about 3 to below 7, about 4 to below 7, about 2 to about 6, about 3 to about 6, or about 4 to about 6.

According to a yet further aspect of the invention there is provided a kit for colouring hair, said kit comprising:
a composition comprising dihydroxyacetone (DHA), in free form or in salt form;
optionally an applicator for the DHA composition; and
means for heating the treated hair.

As hereinbefore described, the means for heating the treated hair should be capable of heating the treated hair to a temperature of from about 100° C. to about 250° C. The means for heating the treated hair may comprise, for example, a hot iron, such as, a curling iron, a straightening iron, or a hot comb, and the like.

The present invention will now be described by way of example only, with reference to the following examples.

The following experiments were carried out using DHA suitable for cosmetic use.

EXAMPLE 1

10% w/v solution of DHA was applied to skin and different hair types (white and 50% grey) for 16 hours at room temperature/body temperature.

Result

Colour change on skin was observed within 2 hours, no change in hair colour after 16 hours.

EXAMPLE 2

DHA (6.0%) was formulated into a gel and cream, applied to hair samples (bleached, white, 50% & 90% grey) and kept at room temperature and 40° C. for 24 hours.

Result

No colour change with either gel or cream formulation at room temperature. Noticeable colour change in samples kept at 40° C.

EXAMPLE 3

DHA (6.25%) solution was applied repeatedly to hair samples (bleached, blonde, 90% grey) for 5 minutes every 24 hours. After application, the hair fibres were treated in different ways (A-D)
A Blow dry
B Blow dry+thermal straightening (200° C.)
C Shampoo/conditioner+blow dry
D Shampoo/conditioner+blow dry+thermal straightening (200° C.).

Result
A Samples noticeable change colour after 5 applications.
B Samples change colour immediately.
C Samples noticeable change colour after 5 applications.
D Samples change colour immediately.

EXAMPLE 4

DHA solution (1.0-6.0%) was applied to hair samples (bleached, white, 90% grey) for 5 minutes, then blow dried and thermally straightened (200° C.).

Result

Immediate colour change in all samples, darkening with increasing % inclusion.

EXAMPLE 5

Wash-fastness of hair treated once with DHA solution (2.0, 4.0, 6.0% w/w) for 5 minutes, blow dried, and thermally straightened (200° C.).

Result

Shows good, consistent wash-fastness up to 8 washes—some loss in colour.

EXAMPLE 6

Indigo (25%) and DHA (6.25%) were mixed into a paste, left to develop for 30 minutes, applied to white hair for 1/⅔ hours, rinsed, blow dried, and straightened (240° C.).

Result

New colour different to indigo used on its own.

EXAMPLE 7

Indigo (10, 15, 25%) was mixed into a paste, left to develop for 1 hour, applied to hair (bleached, white, 90% grey) for 1 hour, rinsed, blow dried, and straightened (240° C.). Colour was left to develop or 24 hours, after which a solution of DHA (6.25%) was applied for 5 minutes, blow dried, and straightened (240° C.).

Result

Get a purple/brown colouration after application of heat, which darkens slightly after 24 hours from application of DHA solution.

EXAMPLE 8

Henna (25%) and DHA (6.25%) were mixed into a paste, left to develop for 1 hour, applied to white hair for 1/⅔ hours, rinsed, blow dried, and straightened (240° C.).
Result
New colour different to henna used on its own.

EXAMPLE 9

Henna (5%), indigo (10%), and DHA (6.25%) were mixed into a paste, left to develop for 1 hour, applied to white hair for 1/⅔ hours, rinsed, blow dried, and straightened (240° C.).
Result New colour different to henna/indigo used on their own in that ratio.

EXAMPLE 10

Nisarg blends; Sienna; Copper; Caramel; and brown, were mixed with water (different ratios) into a paste, left to develop for 1 hour, applied to hair (bleached, white, 90% grey) for 1 hour, rinsed, and blow dried. Colour was left to develop or 24 hours, after which a solution of DHA (6.25%) was applied for 5 minutes, blow dried, and straightened (240° C.).
Result
After application of the DHA solution, all the hair samples darkened.

EXAMPLE 11

DHA solution (6.00%) was applied to hair samples (bleached, white, 90% grey) for 5 minutes, then blow dried and thermally straightened at varying temperatures—in order to gauge the minimum temperature needed to induce an immediate colour change.
Result
Varying degrees of colouration with different applied temperatures. Colour change begins at 120° C., and the colour darkens with increasing temperature.

EXAMPLE 12

Nisarg blends; Sienna; Copper; Caramel; and brown, were mixed with water and conditioner (different ratios) into a paste, left to develop for 1 hour, applied to hair (white, bleached, 90% grey) for 1 hour, rinsed, and then blow dried.
The blend dyed hair samples were treated with DHA solution (4%) for 5 min, dried and then straightened (240° C.).
Wash Fastness was carried out on those samples in order to compare water and conditioning liquid effects with the addition of DHA.
Result
Regardless of the whether the natural dye blends were mixed with water or conditioning liquid, the addition of DHA improves wash-fastness across all the blend colours (Lower ΔE*, ΔL*, Δa*, and Δb*).

EXAMPLE 13

DHA solution (1.00-6.25%) was applied to oxidatively dyed hair for 10 seconds, and then blow dried and thermally straightened (240° C.).

Wash fastness was carried out on those samples in order to compare change in colour with washing between an oxidatively dyed hair sample and an oxidatively dyed hair sample treated with DHA.
Result
Regardless of the concentration of DHA applied, wash-fastness is improved; showing increasing improvement with increasing concentration of DHA.

The invention claimed is:

1. A method for colouring hair, said method comprising treating hair with a composition comprising dihydroxyacetone (DHA), in free form or in salt form; optionally drying the hair; and heating the treated hair, including the applied DHA composition, to a temperature of from about 100° C. to about 250° C.;
provided that said composition does not include additional colorants.

2. The method according to claim 1 which comprises applying the DHA composition to select portions of the hair.

3. The method according to claim 1 which comprises applying the DHA composition to all of the hair of the head.

4. The method according to claim 1 wherein the DHA composition is applied to dry hair, wet hair or damp hair.

5. The method according to claim 1 wherein the hair is shampooed or rinsed prior to the application of the DHA composition.

6. The method according to claim 1 wherein heat is applied to the DHA treated hair within about 5 minutes after application of the DHA.

7. The method according to claim 1 wherein the treated hair is heated for a time period from about 1 minute to about 60 minutes.

8. The method according to claim 1 wherein a hot iron is used to apply heat to the treated hair.

9. The method according to claim 8 wherein the hot iron is selected from the group consisting of a curling iron, a straightening iron or a hot comb.

10. The method according to claim 1 wherein after the heating is complete, the hair is rinsed or shampooed as desired.

11. The method according to claim 1 wherein the amount of DHA, in free form or in salt form, present in the composition is from about 1 to about 20% w/w.

12. The method according to claim 1 wherein the DHA composition is oil based or is an aqueous solution.

13. The method according to claim 1 wherein the DHA composition includes one or more water-soluble solvents.

14. The method according to claim 13 wherein the one or more water-soluble solvents is selected from the group consisting of glycerin, mono-alcohols, polyols (polyhydric alcohols), glycols, and mixtures thereof.

15. The method use according to claim 1 wherein the DHA composition includes one or more thickening agents.

16. A kit for colouring hair, said kit comprising:
a composition comprising dihydroxyacetone (DHA), in free form or in salt form; provided that said composition does not include additional colorants;
optionally an applicator for the DHA composition; and means for heating the treated hair.

17. A kit according to claim 16 wherein the means for heating the treated hair is capable of heating the treated hair to a temperature of from about 100° C. to about 250° C.

* * * * *